Dec. 1, 1942. K. A. LUCAL Plant Pat. 556
BUDDLEIA PLANT
Filed Dec. 10, 1941
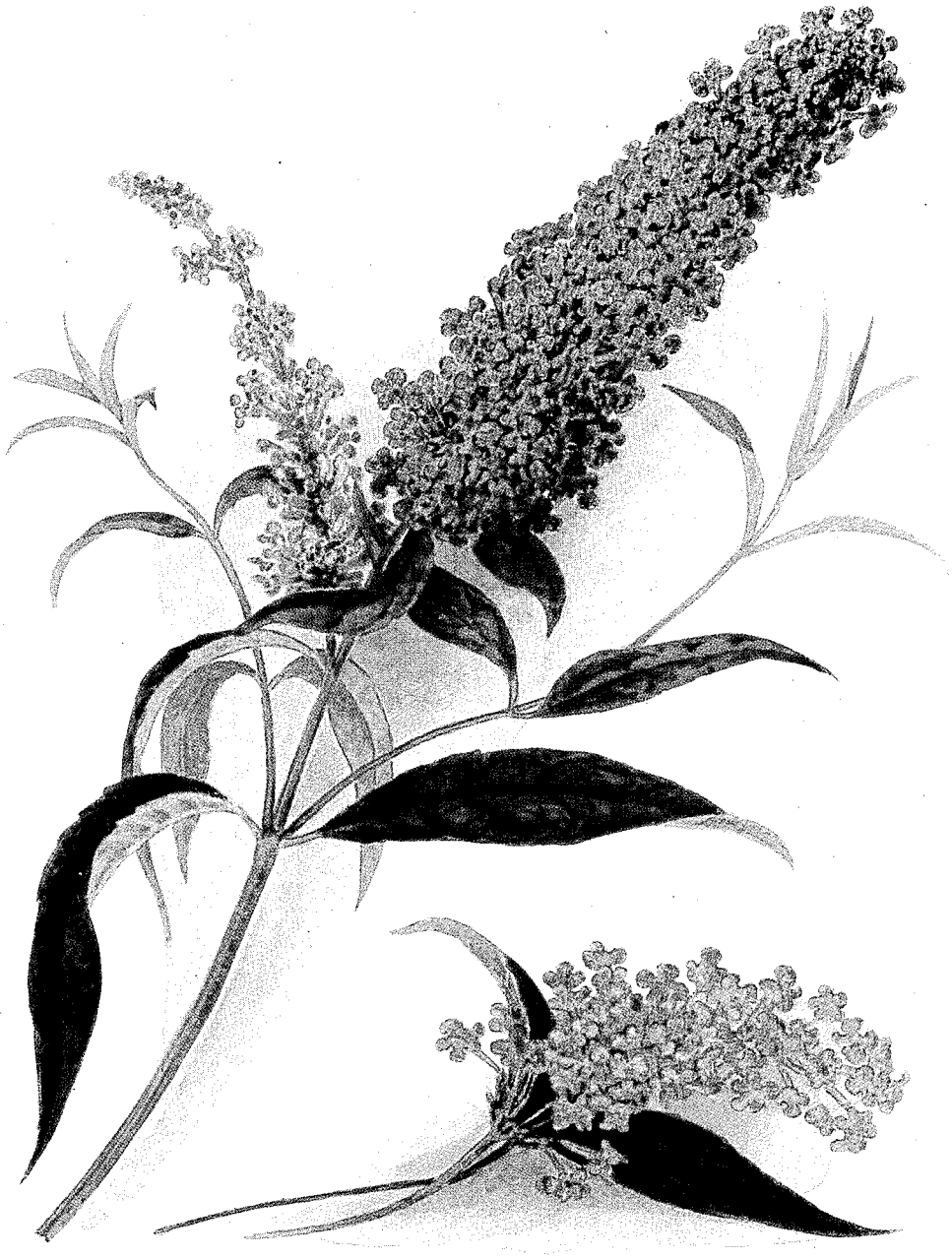
Inventor
Karle A. Lucal
Witness
Addison E. Avery
Rummler Rummler & Davis
Attys.

Patented Dec. 1, 1942

Plant Pat. 556

UNITED STATES PATENT OFFICE

556

BUDDLEIA PLANT

Karle A. Lucal, Springfield, Ohio, assignor to Good & Reese, Inc., Springfield, Ohio, a corporation of Ohio Application December 10, 1941, Serial No. 422,366

1 Claim. (Cl. 47—60)

The new variety of Buddleia plant herein described and illustrated is a cross between an unnamed seedling and B. Royal Purple, which was made in 1938 at Springfield, Ohio. This new variety has been reproduced by cuttings through several generations and its characteristics appear to be permanently fixed.

The primary object in carrying out this invention was to fix the peculiar warm or reddish cast in color of this Buddleia, which is largely the distinguishing characteristic of the new variety. Another object was to produce a fuller and larger panicle, more circular in shape than the ordinary Buddleia.

This new variety in plant structure is similar to the parent, B. Royal Purple. The flower has the usual tubular, four-lobed corolla. The leaves of the plant are short petioled and arranged opposite each other on the stem.

The accompanying illustration shows in full color a typical branch of full-blown blossom, buds, and, at the bottom, a bloom under Mazda light.

The flower head presents a distinctive pyramid of amaranth purple color which is made more conspicuous by the deeper reddish color of the mass as a whole. The entire cluster blooms at substantially the same time. The long, full panicles on the upright sturdy stems are outstanding and noticeable.

The plant has a thick, sturdy stem substantially four-sided, with a brownish tinge. The leaves are a dark green in color with a silvery green under surface, lanceolate in shape and glabrous. The plant as a whole has a trim, well-proportioned appearance.

The following is a detailed description of the new variety:

*Bush*

Size: 4 to 6 feet.

Leaves: Glabrous. Heavy—normal.

*Length.*—4 to 5 inches.

*Quality.*—Leathery.

*Color.*—Upper surface, dark green. Under surface, silvery green.

*Shape.*—Lanceolate.

Stems: Erect, sturdy, substantially four-sided.

*Growth.*—Heavy.

*Length.*—5 to 6 feet.

*Colors.*—New, green. Old, brown.

*Texture.*—New, smooth. Old, smooth.

Branches (angle of attachment): 45°.

Twigs: 45°.

*Flower*

Buds: Formed in summer.

Bloom:

*Color.*—Amaranth purple.

*Formed.*—In panicles or clusters, very full.

Seeds:

*Size.*—¼ in. in length.

*Shape.*—Long, narrow and winged.

*Number.*—25 to 75 per pod.

*Color.*—Brown.

Ripening period: September—October.

The color designations according to "A Dictionary of Color by Maerz and Paul" are as follows:

| | Color | Plate | Letter | No. |
|---|---|---|---|---|
| Main body of flower (top or face). | | 41 | L | 8 |
| Tube or base | Amaranth Pr. | 53 | L | 3 |
| Center eye | Nasturtium. | 4 | I | 12 |
| Change of color under Mazda light of body of flower. | | 3 | L | 4 |
| Face or body leaf color | Mt. Vernon green | 23 | J | 8 |
| Back of leaf | | 19 | B | 4 |
| Small tip buds | Water green. | 19 | C | 2 |
| Stem: Marked with | | 14<br>48 | C<br>J | 3<br>1 |

This new variety of Buddleia is easily distinguished from other varieties by its unusual coloring and fullness of bloom.

Having thus disclosed the invention, I claim:

A new and useful variety of Buddleia plant with features in combination substantially as shown and described, characterized particularly by unusual amaranth purple color of its blossoms, fullness of bloom, clean-cut appearance of the plant as a whole, and sturdy stems.

KARLE A. LUCAL.